United States Patent [19]

Mata et al.

[11] Patent Number: 5,393,161
[45] Date of Patent: Feb. 28, 1995

[54] EXTERNAL FIXATOR

[75] Inventors: Jacques Mata, Etoy; Marcel Wagenknecht, Le Lignon, both of Switzerland

[73] Assignee: Jaquet Orthopedie S.A., Geneva, Switzerland

[21] Appl. No.: 127,963

[22] Filed: Sep. 28, 1993

Related U.S. Application Data

[63] Continuation of Ser. No. 803,924, Dec. 9, 1991, abandoned.

[30] Foreign Application Priority Data

Dec. 10, 1990 [CH] Switzerland .................. 3891/90

[51] Int. Cl.⁶ .................. F16B 7/00; A61B 19/00; A61B 17/56
[52] U.S. Cl. .................. 403/133; 403/113; 403/112; 403/132; 403/141
[58] Field of Search .................. 606/53–59; 403/24, 112–115, 122, 124, 128, 131, 132, 141, 142, 133

[56] References Cited

U.S. PATENT DOCUMENTS

| | | | |
|---|---|---|---|
| 2,346,346 | 4/1944 | Anderson | 606/59 |
| 4,127,119 | 11/1978 | Kronner | 606/59 |
| 4,135,505 | 1/1979 | Day . | |
| 4,312,336 | 1/1982 | Danieletto et al. . | |
| 4,620,533 | 11/1986 | Mears . | |
| 4,621,627 | 11/1986 | De Bastiani | 606/57 |
| 4,757,809 | 7/1988 | Koeneman | 606/59 |
| 4,890,631 | 1/1990 | Hardy | 606/59 |
| 4,895,141 | 1/1990 | Koeneman | 606/59 |
| 4,941,481 | 7/1990 | Wagenknecht . | |
| 5,019,077 | 5/1991 | De Bastiani | 606/59 |
| 5,098,432 | 3/1992 | Wagenknecht . | |

FOREIGN PATENT DOCUMENTS

| | | | |
|---|---|---|---|
| 227594 | 7/1987 | European Pat. Off. | 606/53 |
| 393346 | 10/1990 | European Pat. Off. | 606/54 |
| 984468 | 1/1983 | U.S.S.R. | 606/59 |

Primary Examiner—Randolph A. Reese
Assistant Examiner—Anthony Knight
Attorney, Agent, or Firm—Peter C. Richardson; Lawrence C. Akers; Raymond W. Augustin

[57] ABSTRACT

By virtue of its modular construction, this external fixator makes it possible to position the pins (21 to 25) in the bone fragments (11 to 13) taking account of anatomical criteria. The pins are at least indirectly integral with universal joints (36 to 38) with balls (46 to 48) permitting the orientation of the pins relative to connecting bars 503 and 504. The external fixator additionally comprises connecting pieces for articulation between the connecting bars (501 to 507), such as the articulation (7), the telescopic connecting piece (8) and orientable connecting pieces (97 to 99). After the onset of osseous consolidation, some of the connecting bars and their connecting pieces can be removed, it being possible for the bars (501,502) to be withdrawn from the vices (65, 66).

14 Claims, 4 Drawing Sheets

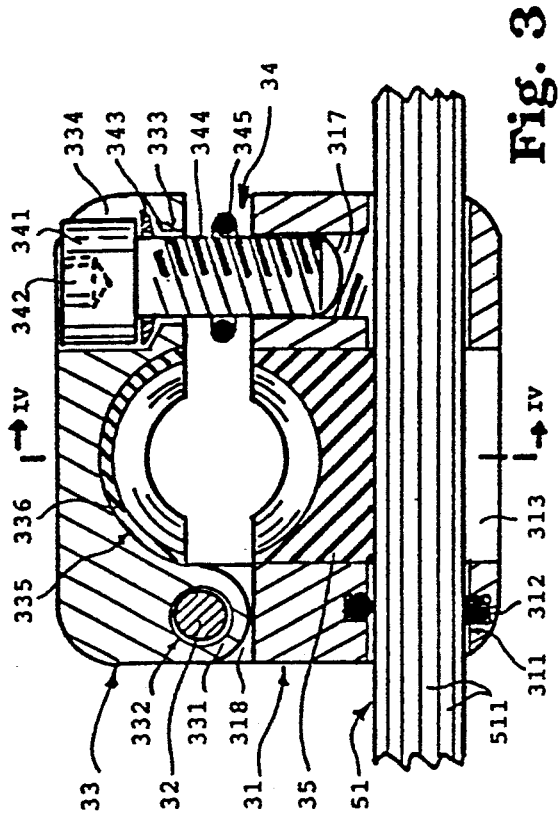
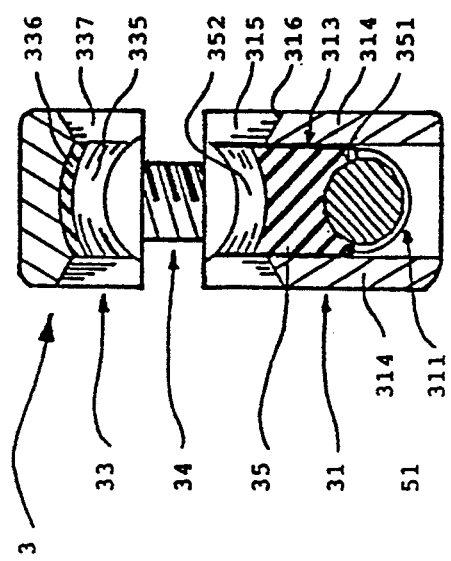
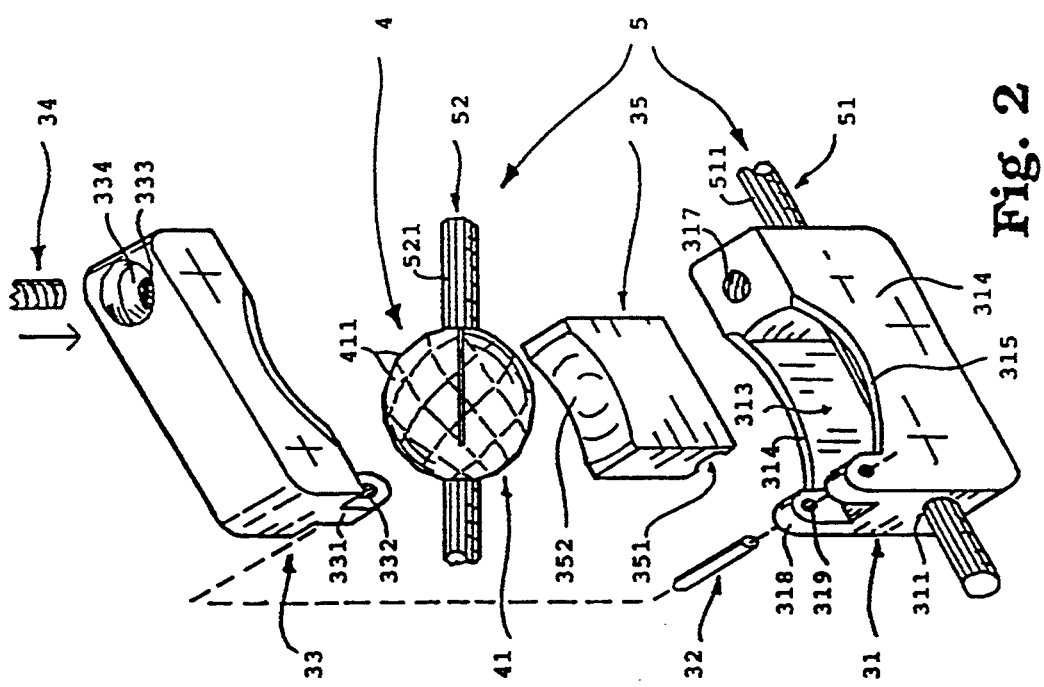
Fig. 3
Fig. 4
Fig. 2

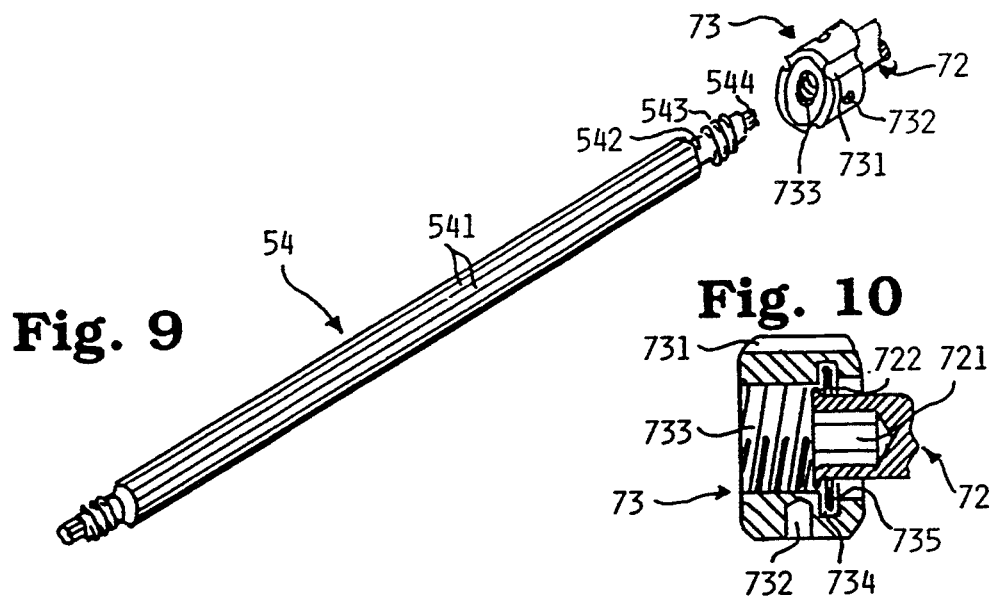
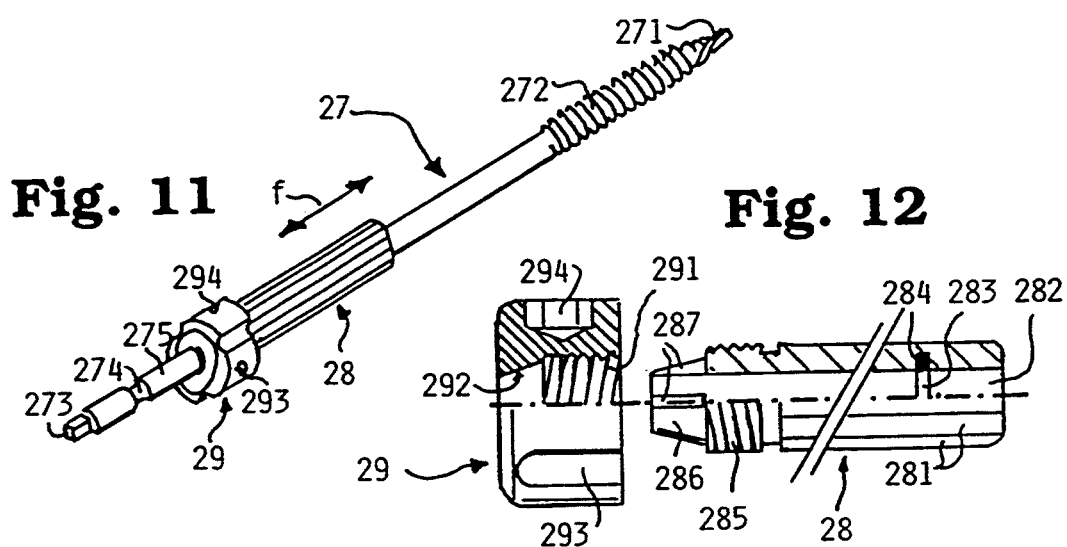
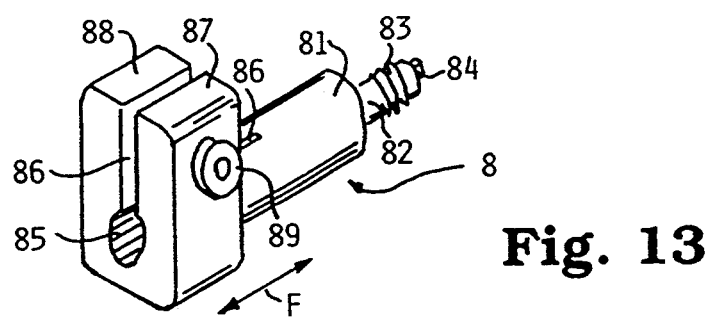

EXTERNAL FIXATOR

This is a continuation of application Ser. No. 07/803,924, filed on Dec. 9, 1991, now abandoned.

The present invention relates to the field of health and concerns more specifically an external fixator for bones or bone fragments which is used in traumatology.

For a long time now, external fixators have been developed which comprise pins which are inserted into the bone fragments and are connected to a frame or to one or more connecting bars. In most cases, and in order to guarantee maximum stability, it is customary to arrange at least two pins on each side of the fracture. The pins are generally inserted depending on the position in which it is intended to fit the frame of the fixator relative to the limb which is to be treated. They are often arranged using a drilling jig corresponding to the vise intended for clamping the pins. Consequently, the pins are sometimes introduced into regions of the body which the practitioner would prefer to avoid, because they are too close to nerves or arteries, for example.

The present invention aims to overcome this disadvantage and proposes an external fixator which can be used regardless of the positions of the pins which have been inserted beforehand in the bone fragments, passing through preferred regions. The fixator comprises a universal joint making it possible to orient the pins relative to the connecting bars with a greater degree of freedom. By virtue of the components, which will be described hereinbelow, the practitioner can first of all position the pins as a function of the configuration of the fracture, on the one hand, and in accordance with the anatomy of each patient, on the other hand. Only then will he put into position the components forming the external fixator assembly.

These components are designed to be placed with respect to the pins which have been inserted beforehand in the bone fragments, and authorize to modify at will the number of connecting bars. With the universal joint according to the invention, one can easily substitute the ball in view of the wanted final configuration. Furthermore a unique tightening operation immobilizes the connecting bars with respect to the pins or to the other bars.

The fixator according to the invention comprises:
- pins inserted into the bone fragments,
- one or more positioning bars constituting the outer frame of the fixator,
- one or more connecting pieces for articulation between the bars and the pins or the bars. The fixator is characterized in that the pins are at least indirectly integral with a universal joint with a removable ball capable of ensuring the independent positioning of the pins relative to one of the said bars.

In a preferred embodiment, the universal joint consists of:
- a partially spherical body constituting a ball,
- a first part provided with a first hollow of general spherical shape,
- a second part provided with a longitudinal passage and a clearance facing the first hollow,
- a blocking element provided with a second hollow of general spherical shape and arranged in the said clearance,
- at least one locking screw arranged substantially perpendicular to the said longitudinal passage and able to block at one and the same time the ball and the cylindrical piece (bar or pin) introduced into the longitudinal passage.

With such a device the practitioner positions the pins, inserted in bone fragments, taking account only of anatomical criteria, then he holds these pins in a universal joint according to the invention, either directly or in a intermediate vice, and chooses the type of ball to be used, before positioning the connecting bars and reducing the bone fracture under X-ray. He can further strengthen the stability of the fixator by supplementary bars and connecting pieces, which can be partially withdrawn after the onset of osseous consolidation.

The accompanying drawings illustrate, by way of non-limitative examples, some embodiments of the present invention.

FIG. 2 is a view, in exploded perspective, of a universal joint for the orientation and fixation of two cylindrical pieces.

FIG. 3 is a longitudinal cross-sectional view of the joint in FIG. 2.

FIG. 4 is a transverse cross-section of the joint along IV—IV in FIG. 3.

FIG. 9 is a perspective view of a connecting bar and of a bolt for fixing another component.

FIG. 10 is a longitudinal cross-section of the bolt in FIG. 9.

FIG. 11 is a perspective view of a bone pin, provided with a clamping chuck.

FIG. 12 shows the components of the chuck in FIG. 11, seen in longitudinal cross-section in the upper half and laterally in the lower half of the drawing.

FIG. 13 is a perspective view of a telescopic connection of two cylindrical pieces placed end to end.

Figure 1:
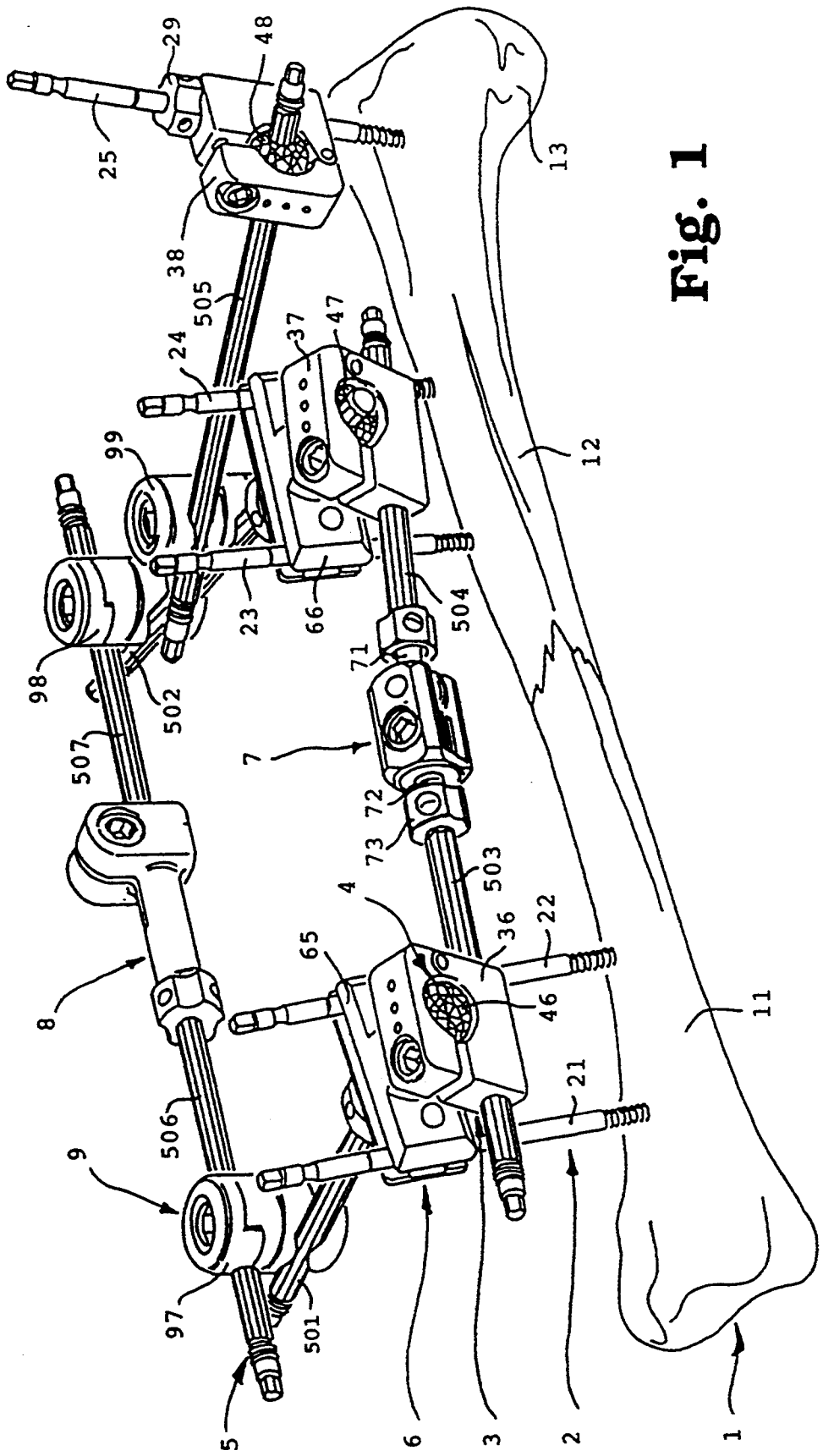
FIG. 1 is a schematic view of a fixator used in an assembly on a long bone and comprising universal joints according to the invention.

In the general view of a fixator in FIG. 1, a bone 1 has been shown, in which pins 2 are inserted. The fixator comprises universal joints 6 comprising balls 4 and intended for the orientation, at least indirectly, of the pins relative to the bars 5 forming the frame of the fixator. It is possible in addition to use a vice 6 for clamping the pins, as well as different connecting pieces arranged between the bars, such as an articulation 7, a telescopic connecting piece 8 and an orientable connecting piece 9.

It will also be seen in FIG. 1 that the bone 1 is fractured in two fragments 11 and 12, receiving, respectively, pins 21, 22 and pins 23 to 25.

Both pins 21 and 22 are clamped in a vice 65 of which one jaw cooperates with a ball 46 clamped in the universal joint 36, and of which the other jaw is integral with a connecting bar 501 held in an orientable connecting piece for positioning 97. Similarly, pins 23 and 24 are fixed in a vice 66 cooperating on the one hand with the ball 47 of a universal joint 37 and on the other hand with a connecting bar 502 held in an orientable connecting piece 98. It should be noted that the ball 46 is arranged at the end of a bar integral with the vice 65, whereas the ball 47 has a central passage for the connecting bar for the vice 66, which makes it possible to adjust the distance between the joint and the vice. As will be seen in greater detail hereinbelow, longitudinal passages made in the joints 36 and 37 receive the positioning bars 503 and 504 which are orientable relative to one another by virtue of the device 7 for articulation and blocking. The pin 25 is inserted in the epiphysis 13 and is directly fixed in the universal joint 38, of which the spherical body 48 is able to block a bar 505 which completes the frame of the fixator by being connected to the bar 502 by means of orientable connecting piece 99.

Alternatively, the vices 65 and 66 could be omitted and each pin 21 to 24 could be fixed directly, similarly to that shown by reference number 25, in a universal joint which would be fitted along the bars 503 or 504.

Between the orientable connecting pieces 97 and 98 a bar is shown for strengthening the assembly, which bar can be removed after the onset of consolidation of the fracture. In FIG. 1, a bar is shown in two parts 506 and 507 separated by a telescopic connecting piece, in order to show the latter in a general view, although it is not compulsory in this configuration in which the bar length can be adjusted with respect to the orientable connecting pieces 97 and 98.

In order to ensure optimum blocking of the components shown, bars of polygonal cross-section will preferably be used, so that their many faces prevent any rotation of the bars on their axis. For the same purpose, the spherical parts of the balls will comprise facets, as will be seen hereinbelow in the detailed description of the various components. Alternatively, it would be possible to used bars of circular cross-section and smooth balls, of which the outer surfaces would be covered with an anti-slip coating.

The universal joint 3 shown in detail in FIGS. 2 to 4 consists of a body 31 receiving a shaft 32 on which is articulated an upper jaw 33 intended to hold the ball 41 when the screw 34 is tightened. For purposes of clarity of the drawing, the ball 41 and the connecting bar passing through it are not shown in FIGS. 3 and 4.

The body 31 is of general parallelepipedic form. It comprises a longitudinal passage 311 of circular cross-section, in which a connecting bar 51 can be introduced. As can be seen in the cross-section in FIG. 3, an O-ring seal 312 is arranged in a groove designed for this purpose; the O-ring seal is intended to retain the bar 51 while at the same time permitting its free positioning relative to the universal joint during the reduction of the fracture.

The body 31 moreover has an internal clearance 313 intended to receive a blocking element 35 held between side wings 314. At the top, the wings 314 present a rounded clearance 315 (FIG. 2) ending in a bevel 316 (FIG. 4). In its upper part, the body 31 has a tapped opening 317 perpendicular to the passage 311 and intended to cooperate with the screw 34, as well as two lugs 318 provided with passages 319 for holding the shaft 32.

The upper jaw 33 is also of general parallelepipedic form. In its lower part, it comprises, at one end, a projection 331 provided with a transverse passage 332 for the shaft 32 and, at the other end, an opening 333 in line with the tapped opening 317 receiving the locking screw 34 whose head 341 is sunk in a clearance 334. The lower part of the jaw 33 further comprises a hollow of spherical curvature 335 intended to receive the ball 41. A coating 336 is applied in this hollow 335 in order to promote the fixation of the ball: the coating consists of a flexible elastic layer or is produced by a surface treatment. FIG. 4 shows the rounded bevelled clearances 337 designed to leave a free passage for a connecting bar 52 passing through the ball 41, similar to the rounded areas 315 of the body 31.

The clamping means of the universal joint consist of the screw 34 whose head 341 is provided with an opening 342 intended to receive a clamping tool, for example a hexagon tool. The head 341 bears on a washer 343 intended to cooperate with the bottom of the clearance 334 and its threaded part 344 engages in the tapping 317 of the body 31. In addition, an O-ring 345 can be arranged on the threading 344 between the body 31 and the jaw 33 in order to retain the screw 34 when it is not engaged in the tapping 317.

The blocking element 35 is intended to cooperate on the one hand with the ball 41 and on the other hand with the connecting bar 51. For this purpose it presents, along its entire length, a semicylindrical clearance 351 in its lower part and a hollow 352 of spherical shape in its upper part. The clearance 351 is dimensioned so as to correspond to the cross-section of the bar 51, and the hollow 352 corresponds to the curvature of the ball 41. Thanks to the blocking element 35 which simultaneously acts on the ball 41 and on the connecting bar 51, these pieces can be positionned and secured in a unique operation while acting on the screw 34.

In order to increase the attachment between these pieces, it will be noted that the bar 51 consists of a twelve-sided cylinder 511 and that the ball has a series of facets 411, such that their ridges can become embedded in the blocking element 35 which is made of a material which is less hard than those of the ball and the connecting bar. Alternatively, these ridged elements can be replaced by an anti-slip coating formed, for example, of microspheres arranged on a bar of circular cross-section or a perfectly spherical ball.

In the alternative shown in FIG. 2, the ball 41 is passed through by a connecting bar 52. Referring to the detailed view of the ball in FIGS. 5 and 6, it will be noted that the ball 41 has a central passage 412 intended to receive with play a connecting bar of dodecagonal cross-section. For this purpose, the central passage 412 comprises flutings 413 corresponding to the faces 521 of the connecting bar 52. It will be noted in the cross-section in FIG. 6 that a groove 414 receives an O-ring 415 intended to hold the bar 52 as long as the ball 41 is not clamped in the universal joint in FIG. 2.

The ball 41 is provided with three radial slots 416 and 417 spaced uniformly over its periphery and intended to give elasticity to the ball. The slot 416 is made across the entire length of the ball, whereas the slots 417 extend across part of its length, bridges 418 and 419 holding together the segments constituting the ball. An alternative possibility would be an even number of slots 417 arranged alternating on one side or the other over the periphery of the ball.

Figure 7:
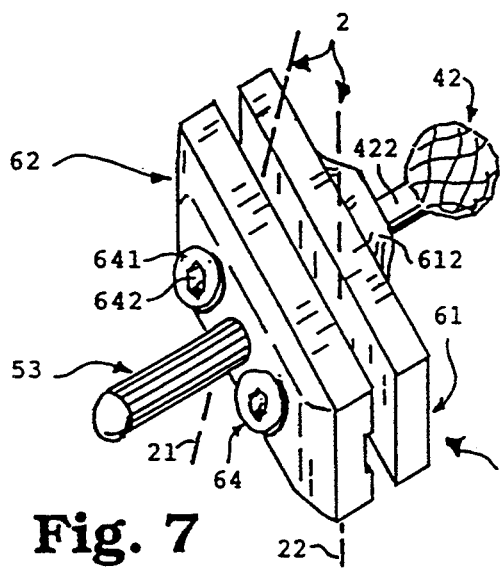
FIG. 7 is a perspective view of a vice for orientation and clamping of the bone pins, which is used together with the universal joint according to the invention.

The universal joint in FIGS. 2 to 4 can also receive a ball directly formed at the end of a connecting bar, as shown schematically in FIG. 1. Depending on the requirements, it can also hold a ball fixed to another component of the external fixator, such as the vice 6 for orienting and clamping the bone pins, as detailed in FIGS. 7 and 8.

The vice 6 consists of two jaws 61 and 62 of general parallelepipedic form intended to clamp the bone pins 21 and 22. It should be noted that the faces 611 and 621 of the jaws 61 and 62 facing each other are plane so as to make it possible to hold pins 21 and 22 which are not arranged in parallel.

The jaw 61 comprises on its outer face a boss 612 having a passage 613 intended for the fixation of a ball 42. In this alternative, the ball 42 having blocking facets 421 is formed at the end of a bar 422 fixed in the central passage 613 by adhesion, welding or other means. Alternatively, and in order to make it possible to modify the length of the bar 422, it is possible to provide for a removable fixation of the ball 42 in the jaw 61. The latter additionally has two tapped openings 614 intended to receive the means for clamping the vice.

The jaw 62 comprises an opening 622 in which a connecting bar 53 is fixed. The length of the latter will be chosen depending on the requirements, and in addition, as will be seen hereinbelow, it may be advantageous to remove it during the course of treatment. The bar 53 is therefore preferably screwed and pinched by a counternut 623, shown by broken lines in FIG. 8. The jaw 62 also has two passages 624 with external clearances 625 for the means 64 for clamping the vice. The distance between the passages 624 is therefore the same as that between the tapped openings 614.

The clamping means 64 consist of two screws, of which the head 641 is provided with an opening 642 intended to receive a clamping tool, for example a hexagonal tool. Each head 641 bears on a washer 643 intended to cooperate with the bottom of the clearance 625, and its threaded part 644 engages in the tapping 614 in the jaw 61.

Figure 8:
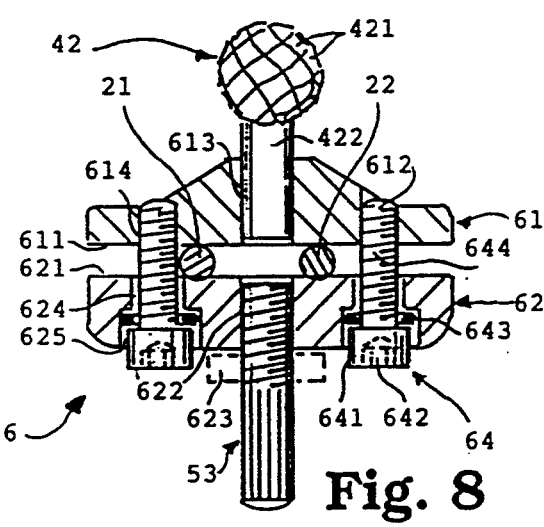
FIG. 8 is a longitudinal cross-section of the vice in FIG. 7.

In FIG. 8, a bar 53 has been shown whose free end is rounded. Alternatively, there may be inserted in the vice a bar provided with fixation means at the end, such as those which will be described with regard to the bar 54 in FIG. 9.

Figure 5:
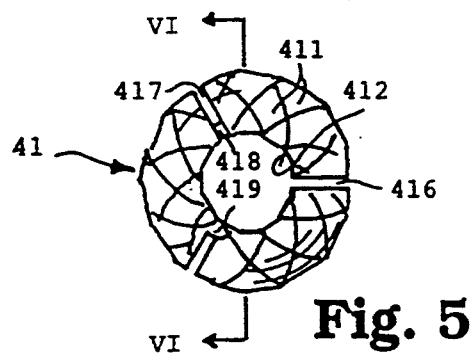
FIG. 5 is an end view of the ball used in the joint in FIG. 2.
Figure 6:
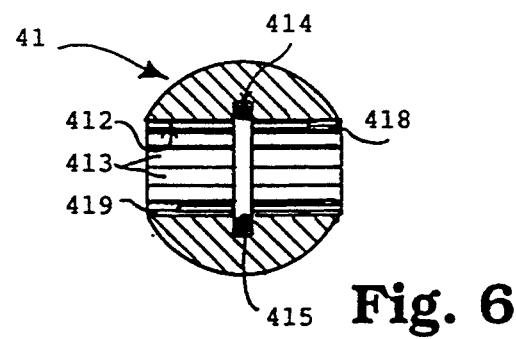
FIG. 6 is a longitudinal cross-section along VI—VI in FIG. 5.

Like the connecting bars described hereinabove, this bar 54 is of dodecagonal cross-section and has sides 541 intended to cooperate, for example, with the blocking element 35 in FIGS. 2 to 4 or with the flutings 413 made in the ball 41 in FIGS. 5 and 6. In order to permit its end connection to the fixator elements described here, at least one of its ends comprises a narrowing 542 provided with a threading 543, ending in an extension of square or hexagonal cross-section 544 intended to cooperate with a corresponding opening in an adjacent piece 72, in order to prevent any rotation of the connecting bar about its axis.

Connecting bars of different standard lengths, for example multiples of 5 cm, will preferably be used in order to adapt the fixator to each specific application.

The articulation 7 shown in the general view in FIG. 1 is intended to ensure the relative orientation of two bars 503 and 504 connected to the articulation by means of cylindrical connecting pieces 71 or 72 and fixed by means of nuts 73. In the alternative shown in FIGS. 9 and 10, the cylindrical piece 72 has at its free end a central clearance 721, of a shape corresponding to the extension of square or hexagonal cross-section 544 of the connecting bar 54, and terminates in an outer flange 722 intended to hold the nut 73.

The nut 73 has on the outside flutings 731 between which there are provided openings 732 intended to receive a clamping tool, for example a hexagonal tool. The nut 73 has on the inside a tapping 733 corresponding to the threading 543 of the connecting bar and a groove 734 able to receive a clip 735 dimendioned in such a way that it is held by the flange 722. Alternatively, the clip 735 can be replaced by a set of balls introduced via a passage made radially in the nut 73.

The pins inserted in the bones and used in the fixator according to the invention can be self-tapping pins, like the pin 27 shown in detail in FIG. 11. Each pin comprises a tapping end 271, followed by a threading 272 intended to hold it in the bone fragment. Its opposite end finishes with a square 273 intended to cooperate with a tool making it possible to effect the rotations necessary for inserting the pin in the bone. A clearance 274 is provided on the smooth part 275 of the pin in order to allow it to be held in a mandrel.

In the alternative in FIG. 11, an intermediate chuck 28 is provided on the smooth part 275 of the pin so as to bring the diameter of the latter to that of the connecting bars 51, 52, etc., so that the components of the fixator are modular. The chuck 28 consists of a tube having on the outside twelve sides 281 corresponding to the sides 511, 521, 531 or 541 of the bars already described. On the inside, the chuck comprises a central passage 282 of circular cross-section intended to receive the smooth part 275 of the pin. The passage 282 has a groove 283 receiving an O-ring 284 intended to hold the pin 27 in place as long as the chuck is not clamped. One of the ends of the chuck comprises a threading 285 finishing in a frustoconical part 286 having radial slots 287 spaced uniformly over its periphery and conferring upon the end of the chuck a certain elasticity. The threading 285 is intended to cooperate with the nut 29 and more particularly with its tapping 291. The bottom of the nut has a frustoconical clearance 292 intended to cooperate with the frustoconical part 286 of the chuck in order to close the latter on the pin 27. The nut 29 has on the outside flutings 293 allowing it to be clamped by hand, as well as openings 294 intended to receive a clamping tool used upon blocking of the chuck along the smooth part 275 of the pin. It will be noted that it is preferable to use the same clamping tool in these openings 294 as in the openings 732 of the nut 73 for fixation of a bar at the end of the articulation in FIGS. 9 and 10.

The telescopic connecting pieces 8 in FIG. 13 makes it possible to position two connecting bars end to end, at a distance which can be adjusted in the direction of the arrow F so that the bars forming the fixator do not extend beyond the connecting pieces in which they are fixed. It has a tubular part 81 whose end comprises a narrowing 82 provided with a threading 83, finishing with an extension of square or hexagonal cross-section 84 intended to cooperate with a corresponding opening in the adjacent piece, in order to prevent any rotation of the connecting piece 8 about its axis. The dimensions of the threading 83 and of its extension 84 are the same as those of the threading 543 and the extension 544 of the pin 54, so as to permit connection to other components of the external fixator according to the invention, by means of nuts similar to the nut 73 in FIGS. 9 and 10.

The tubular part 81 comprises at its other end a central opening 85 of dodecagonal cross-section, intended to receive a connecting bar which, in this particular case, can finish with a rounded part, like the bar 53 in FIG. 8.

A slot 86 for elasticity is made on the tubular part 81 and is bordered externally by two extensions 87 and 88 intended to receive clamping means 89 consisting of a screw passing freely in a passage made in the extension 87 and engaging in a tapping formed in the extension 88. It should be noted that the screwhead has the same hexagonal opening as all the previously described elements intended to be clamped.

In one alternative not shown in the drawing, it is possible to arrange at each end of the tubular part 81 a central opening 85 intended to receive a bar, and extensions 87 and 88 capable of being clamped towards one another by clamping means 89.

Of course, in order to avoid injuring the surgeon or the patient, all the components described hereinabove have no sharp edges. The majority of the pieces will be made of light alloy or of composite material in order to make the assembly as light as possible, on the one hand, and so that it is transparent to X-rays on the other hand.

In the course of the operation, the practitioner will begin by inserting the pins in the bone fragments, taking account only of anatomical criteria.

Referring to FIG. 1, the pins will then be clamped either in the vices 65 and 66 (described in detail with reference to FIGS. 7 and 8), or in a universal joint 38, and more specifically in its longitudinal passage after having been introduced into an intermediate chuck 28 (explained in detail with reference to FIGS. 11 and 12) and fixed by means of the clamping nut 29.

Depending on the particular configuration, the type of balls 46 to 48 to be used in the universal joint will then be chosen, before fitting the connecting bars 503 and 504 into position. The fracture will be reduced under X-ray such that the bone fragments recover their normal position. In order to strengthen the assembly in an optimum manner, the frame of the fixator can be further reinforced by bars 501, 502 and 506, 507, and even 505 if necessary, these bars being fixed as shown in FIG. 1 for example, or in any other equivalent manner.

As already been mentioned, it is possible to remove one of the bars after the onset of osseous consolidation, in order to reduce the size and the weight of the assembly, while permitting a slight movement of the bone fragments at the level of the fracture, which movement tends to promote the formation of callus.

It should be noted that, by virtue of the modular construction of all these components described here, one single clamping tool is used for the tightenint of the screws 34, 64, 74, 89 and 96 used in the universal joint 3, the vice 6, the articulation 7, the telescopic 8 and orientable 9 connecting pieces, respectively.

This same tool can be introduced into the openings such as those shown in detail under reference 732 in the cross-section of the nut 73 in FIG. 10. Similarly, the nut 29 for clamping the pin 29 and the various nuts shown schematically in FIG. 1 for the fixation of the bars in the connecting pieces 7 and 8.

We claim:

1. A universal joint to be used as part of an external fixation device, said universal joint comprising:
   a partially spherical shaped body substantially in the shape of a ball, said ball having an outer surface with facets thereon;
   a first part having a first hollow of generally partially spherical shape, said hollow including a flexible elastic layer for engaging said facets on said ball for providing resistance to slipping;
   a second part having a longitudinal passage therein and having a clearance facing said first hollow; and
   a means for pivotally connecting together said first part and said second part, wherein a locking screw arranged in a bore substantially perpendicular to said longitudinal passage is able to hold securely together simultaneously said partially spherical body within said first part and said second part and to hold securely a cylindrical piece to be introduced into said longitudinal passage.

2. A universal joint according to claim 1 and including also a blocking element provided with a second hollow of generally spherical shape and arranged within said clearance within said second part.

3. A universal joint according to claim 2 wherein said means for pivotally connecting said first part and said second part comprises a shaft about which an extension of said first part located opposite said locking screw and an extension of said second part located opposite said locking screw both articulate.

4. A universal joint according to claim 3, wherein said first part and said second part have lateral clearances (337, 315).

5. A universal joint according to claim 2 and including also a cylindrical piece selected from the group consisting of a bar and a bone pin.

6. A universal joint according to claim 5, wherein said blocking element has a face located opposite said second hollow and wherein a longitudinal clearance (351) located on said face opposite said second hollow is able to cooperate with said cylindrical piece (311).

7. A universal joint according to claim 6, wherein said cylindrical piece has an outer surface which is resistant to slipping.

8. A universal joint according to claim 7, wherein said cylindrical has an outer surface having facets thereon for resistance to slipping.

9. A universal joint according to claim 8, wherein said ball has a central passage (412) located therein.

10. A universal joint according to claim 9, and including also a connecting bar and wherein said ball has slots (416, 417) located therein for providing elasticity to said ball.

11. A universal joint according to claim 10, and including also a means of connection for connecting said ball with a vice (6;65, 66) for clamping bone pins.

12. A universal joint according to claim 11, and including also a vice having jaws (61, 62) which serve as means for fixation of a cylindrical body.

13. A universal joint to be used as part of an external fixation device, said universal joint comprising:
   a partially spherical shaped body substantially in the shape of a ball, said ball has an outer surface having facets thereon for providing resistance to slipping;
   a first part having a first hollow of generally partially spherical shape, said hollow including a flexible elastic layer;
   a second part having a longitudinal passage therein and having a clearance facing said first hollow;
   a means for pivotally connecting together said first part and said second part, wherein a locking screw arranged in a bore substantially perpendicular to said longitudinal passage is able to hold securely together simultaneously said partially spherical body within said first part and said second part and to hold securely a cylindrical piece to be introduced into said longitudinal passage;
   a blocking element provided with a second hollow of generally spherical shape and arranged within said clearance within said second part, said means for pivotally connecting said first part and said second part comprising a shaft about which an extension of said first part located opposite said locking screw and an extension of said second part located opposite said locking screw both articulate, said blocking element having a face located opposite said second hollow and wherein a longitudinal clearance located on said face opposite said second hollow is able to cooperate with said cylindrical piece; and wherein said cylindrical piece has an outer surface having facets thereon for resistance to slipping, said ball having a central passage located therein and includes a connecting bar and wherein said ball has slots located therein for providing elasticity to said ball and said joint also including a means of connection for connecting said ball with a vice for clamping bone pins.

14. A universal joint according to claim 13 wherein said vice has jaws which serve as means for fixation of a cylindrical body.

* * * * *